United States Patent [19]
Younes

[11] Patent Number: 5,107,830
[45] Date of Patent: * Apr. 28, 1992

[54] LUNG VENTILATOR DEVICE

[75] Inventor: Magdy Younes, Manitoba, Canada

[73] Assignee: University of Manitoba, Winnipeg, Canada

[ * ] Notice: The portion of the term of this patent subsequent to Sep. 3, 2008 has been disclaimed.

[21] Appl. No.: 501,757

[22] Filed: Mar. 30, 1990

Related U.S. Application Data

[63] Continuation-in-part of Ser. No. 496,172, Mar. 20, 1990, Pat. No. 5,044,362, which is a continuation of Ser. No. 158,752, Feb. 22, 1988, abandoned.

[30] Foreign Application Priority Data

Feb. 21, 1987 [GB] United Kingdom ................ 8704104

[51] Int. Cl.⁵ ............................................. A61M 16/00
[52] U.S. Cl. ......................... 128/204.18; 128/204.21; 128/204.23
[58] Field of Search ..................... 128/204.18, 204.21, 128/204.23, 204.26

[56] References Cited

U.S. PATENT DOCUMENTS

| | | | |
|---|---|---|---|
| 1,406,141 | 2/1922 | Anston | 128/205.18 |
| 3,669,097 | 6/1972 | Fitz | 128/728 |
| 3,985,124 | 10/1976 | Coleman | 128/727 |
| 4,036,221 | 7/1977 | Hillsman et al. | 128/204.23 |
| 4,121,578 | 10/1978 | Torzala | 128/204.23 |
| 4,301,810 | 11/1981 | Belman | 128/200.24 |
| 4,448,192 | 5/1984 | Stawitcke | 128/204.26 |
| 4,459,982 | 7/1984 | Fry | 128/204.23 |
| 4,462,410 | 7/1984 | Blais et al. | 128/727 |
| 4,487,207 | 12/1984 | Fitz | 128/728 |
| 4,587,967 | 5/1986 | Chu et al. | 128/205.18 |
| 4,617,637 | 10/1986 | Chu et al. | 364/505 |
| 4,726,366 | 2/1988 | Apple et al. | 128/205.18 |
| 4,823,788 | 4/1989 | Smith et al. | 128/204.21 |
| 4,957,107 | 9/1990 | Sipin | 128/204.21 |
| 4,971,049 | 11/1990 | Rotariu et al. | 128/204.21 |

FOREIGN PATENT DOCUMENTS

| | | |
|---|---|---|
| 3306607 | 9/1983 | Fed. Rep. of Germany . |
| 2328452 | 10/1976 | France . |
| 1541852 | 3/1979 | United Kingdom . |
| 2054387 | 2/1981 | United Kingdom . |
| 2121292 | 12/1983 | United Kingdom . |

Primary Examiner—Edgar S. Burr
Assistant Examiner—Aaron J. Lewis
Attorney, Agent, or Firm—Sim & McBurney

[57] ABSTRACT

Ventilation to a patient is provided in response to patient effort. The free flow of gas from a piston, or similar air source, in response to patient inhalation is detected, the instantaneous rate and volume of flow are measured and the measurements are used as control signals to a drive motor for the piston to move the piston to generate a pressure which is proportional to the sum of measured and suitably amplified rate and volume of flow signals. Since the command signal to the pressure generator only changes subsequent to, and not in advance of, a change in flow and volume, the ventilator is subservient to the patient and provides a proportional assist to patient ongoing breathing effort during inspiration (Proportional Assist Ventilation, PAV).

16 Claims, 10 Drawing Sheets

――――― Ventilator pressure in absence of effort.

----- Volume and flow in absence of effort

LUNG VENTILATOR DEVICE

REFERENCE TO RELATED APPLICATION

This application is a continuation-in-part of copending U.S. application Ser. No. 496,172 filed Mar. 20, 1990 (now U.S. Pat. No. 5,044,362), which itself is a continuation of U.S. application Ser. No. 158,752 filed Feb. 22, 1988 (now abandoned).

FIELD OF INVENTION

The present invention relates to a method and device to assist in ventilating the lungs of a patient in proportion to patient effort.

BACKGROUND TO THE INVENTION

Ventilators are devices which are used to force gases, usually air or oxygen-enriched air, into the lungs of patients who, for one reason or another, are incapable of sustaining adequate ventilation entirely through their own efforts. The source of pressure may be a piston device, a built in blower or a high pressure line. Commercially-available ventilators utilize various mechanisms to regulate the pressure applied to the patient. In all cases, a breath is triggered which sets in motion a sequence of events during which pressure is applied until a volume or pressure target is reached, at which time the pressure cycle ends. Once the cycle is triggered, the ventilator proceeds in a predetermined manner, set by adjustments of dials on the control panel of the unit. With available devices and methods of ventilation, the ability of the patient to modulate breathing output through his own effort is limited or non-existent, as is apparent from the description below.

One of the principal indications for institution of ventilatory support is the presence of an unfavourable relation between patient effort and resulting ventilation (see FIG. 1). This may be because of neuromuscular weakness, necessitating a greater effort to produce a given pressure, abnormal respiratory mechanics with which greater pressure output is desired to attain a given ventilation, or both. This abnormal relation impairs the patient's ability to control ventilation and breathing pattern in a way that insures optimal $CO_2$ removal and/or oxygenation. In addition, the high respiratory effort results in distress and, if the effort is sufficiently high, may ultimately lead to exhaustion (i.e. respiratory muscle fatigue).

By providing positive pressure at the airway during inspiration, all current approaches to ventilatory support (volume-, pressure- or time-cycled approaches) unload the respiratory muscles and improve the relation between patient effort and achieved ventilation in a global sense. For a given inspiratory effort, the patient receives a greater volume in the assisted breath than he would otherwise. The price of this support, however, is a variable degree of loss of control by the patient over his ventilation and breathing pattern. These effects are illustrated in FIGS. 2 to 4.

With volume cycled ventilation (FIG. 2), the ventilator delivers pressure in whatever amount and time pattern is necessary to cause a predetermined flow pattern and tidal volume to be achieved during the assisted breath. The operator of the ventilator (i.e. physician or therapist), and not the patient, determines the flow and volume to be delivered. If the patient makes an inspiratory effort during the inhalation phase, the ventilator simply decreases the pressure it provides in such a way that the flow and volume delivered are the same as prescribed. The more inspiratory effort the patient makes, the less the pressure delivered by the ventilator (FIG. 2, left to right). Conversely, if the patient does not wish to receive the prescribed volume or flow, and fights back, the machine generates a greater pressure to offset the patient's opposing effort. There results, therefore, an antagonistic relation between patient and machine.

With this volume cycled method of ventilation, the degree of loss of patient control over his own breathing varies, depending on the type of ventilation used. With continuous mandatory ventilation (CMV), loss of patient control is complete, as he not only cannot alter flow and volume within each assisted breath, but also cannot influence frequency. In the assist/control mode (A/C), the patient can alter the frequency of the mandatory breaths, but within each breath, the same adverse relation between patient effort and pressure delivered applies. With the newer synchronized intermittent mandatory ventilation (SIMV), spontaneous breaths are permitted between the mandatory breaths. During these breaths, the patient controls the rate and depth of breathing. However, the abnormal relation between effort and ventilatory output (see FIG. 1) which was the reason for installation of ventilatory support in the first place, continues to apply. In fact, it is worsened by the additional load imposed on the patient by the device and endotracheal tube. The patient, therefore, alternates between breaths in which effort is entirely without ventilatory consequence (mandatory breaths), and breaths in which effort produces abnormally low ventilatory return.

With pressure support methods of ventilatory assist (PS), the delivered pressure is a predetermined function of time, usually an intended square wave pressure beginning at the onset of inspiration and terminating as flow rate declines to a specific amount. The pressure delivered is, therefore, independent of how much inspiratory effort the patient is making during inspiration (see FIG. 3). Any inspiratory effort the patient makes during the breath would produce greater flow and volume (FIG. 3, A to C). However, since the pressure delivered is independent of effort, the ventilatory consequences of patient effort are still subject to the abnormal relation between effort and lung expansion dictated by the disease (FIG. 1). Although the overall relation between effort and ventilation is improved, the ability of the patient to alter ventilation in response to varying needs continues to be impaired. Furthermore, since patient effort normally increases in a ramp fashion during inspiration, while pressure delivered by the ventilator is nearly constant, the ventilator overassists early in inspiration while the assist decreases relatively as inspiration progresses. The patient then would sense an increase in load as inspiration is lengthened and this prompts the patient to breathe with short inspirations, resulting in a small tidal volume.

With airway pressure release ventilation (APRV), pressure at the airway alternates between high and low levels with a time sequence that is independent of patient effort (see FIG. 4). The periodic cycling of pressure insures a minimum ventilation. The patient can also obtain spontaneous breaths independent of the programmed cycles. During these, he receives no assist (i.e., similar to SIMV). The relation between effort and ventilatory consequences during these breaths continues to be poor, as dictated by disease, limiting the patient's ability to alter flow and ventilation in response to varying needs. In fact, since with APRV, operating lung volume is increased, the relation between effort and ventilatory consequences is further compromised on account of the well established adverse effect of increased lung volume on neuromechanical coupling (i.e. pressure generation for a given muscle activation).

I am aware of specific prior art proposals to effect modifications to commercially-available pressure-powered ventilators to allow the pressure produced to vary with electrical activity recorded from a respiratory nerve, as described in Remmers et al, "Servo Respirator Constructed from a Positive-Pressure Ventilator", J. Appl. Physiol. 41: 252 to 255, 1976. To the extent that activity in inspiratory nerves reflects effort these modifications would permit a ventilator to deliver pressure in proportion to effort, as is intended in the present invention. These modifications, which were developed for animal use where inspiratory nerves are accessible and can be recorded from, implicity require direct measurement of inspiratory muscle or nerve activity which is not practical in humans requiring ventilatory support. In contrast, the present invention permits the delivery of pressure in proportion to patient effort without the need for direct recording of activity, and through the use of algorithms that permit the inference of degree of effort from easily measurable variables, such as flow and volume. Poon et al, "A Device to Provide Respiratory Mechanical Unloading", IEEE Trans. Biomed. Eng. 33: 361 to 365, 1986, described a modification to a commercially-available volume ventilator which permits the ventilator to deliver pressure in proportion to inspired flow. Although this device was developed originally to simulate and amplify the effect of helium in reducing respiratory resistance during experimental studies on exercising humans, it can theoretically be used in patients to provide partial ventilatory support. As such, the device would develop pressure with a time pattern that resembles inspiratory flow, which is highest early in inspiration and declines later. Since this pattern is poorly (or even negatively) correlated with patient inspiratory effort, which rises continuously during the inspiratory phase, this pattern of support is quite unlike the method of the present invention, where pressure is intended to be a function of inspiratory effort throughout inspiration, as described in more detail below. Not only is the method completely different (simple resistive unloading vs assist in proportion to effort) but the apparatus described herein is much more suitable for our method (Proportional Assist Ventilation, PAV) than a modification of existing volume ventilators which are designed to regulate flow and not pressure. The design of the invention permits unlimited flow and there is no delay between onset of inspiratory effort and onset of flow from ventilator to patient, since no triggering is required before the gas delivery system is communicated to the patient. The system of the invention also can effect proportional assist through positive pressure at the airway or negative pressure at body surface, whereas a modified positive pressure, gas powered ventilator can serve the former function only.

Some known prior art patents describe a variety of breathing devices. U.S. Pat. No. 3,985,124 describes a spirometer for measurement of the rate and volume of expiratory breathing to create a graphic record of the same. This device possesses an expansible chamber of the piston type which expands in proportion to the exhaled air.

U.S. Pat. No. 3,669,097 describes a device for increasing the capacity and strength of lungs. An expansible bellows chamber is connected to a conduit having a mouthpiece. A selectively-adjustable valve is present in the conduit for constricting the passage from the mouthpiece to the inlet to the bellows chamber, so that a force in excess of the normal pressure developed by the lungs is required to expand the bellows.

U.S. Pat. No. 4,301,810 describes a ventilatory muscle training apparatus comprising a reservoir and a mouthpiece and also having a simple valving system to vent stale air from the reservoir during exhalation and let fresh air into the reservoir during inhalation. The air flow through the mouthpiece is monitored to ensure the intended manner of use of the apparatus is maintained.

U.S. Pat. No. 4,462,410 describes a recording spirometer for performing a breath test which uses a movable pusher plate which is moved in response to the breathing of the patient and a recording medium which enables a record to be made of the volume of air expelled by a patient as a function of time.

U.S. Pat. No. 4,487,207 describes a lung exercise device which has a mouthpiece through which a patient inhales. A conduit connects the conduit to an air inlet and a valve is located in the conduit, normally biased to a closed position. Upon inhaling, the valve is opened and the amount of air inhaled is monitored.

U.S. Pat. No. 4,459,982 by Fry discloses a lung ventilator device which comprises a chamber means which delivers respiratory gases to a patient. This patent describes, as one embodiment, the provision of a flow rate directly controlled by the patient's instantaneous demand under spontaneous breathing of the patient, and hence, at first sight, may be considered relevant to the present invention. However, the operation of the device and its control require movement of the piston in the chamber to maintain the pressure at the patient's airway constant and equal to a reference pressure determined by the operator. Since the device operates to maintain airway pressure constant throughout inspiration, it is apparent that it does not deliver pressure in proportion to patient effort (which varies throughout inspiration), as is the case of the present method (PAV).

British Patent No. 1,541,852 describes a piston, driven by a motor which alters the pressure in the piston according to the power supplied to motor. This system is designed to deliver pressure according to a predetermined pressure-time profile (as in pressure cycled ventilators) or to force a given volume of gas into the patient (as in volume cycled methods). In the method of the present invention, neither pressure nor flow and volume is/are predetermined. Rather, the patient determines his own flow pattern and tidal volume through his own effort, while the ventilator delivers pressure in a manner that parallels the patient's ongoing effort (which is obviously not predetermined).

Other representative prior art employing motor driven pistons that deliver predetermined pressure vs time or volume vs time patterns know to the applicant are Hillman, U.S. Pat. No. 4,036,221, Chu, U.S. Pat. No. 4,617,637 and Apple, U.S. Pat. No. 4,726,366.

Stawitcke (U.S. Pat. No. 4,448,192, U.K. Patent No. 2,121,292) describes a system with motor driven pistons and extremely complex controls, the intent of which are to reduce conflict between patient and ventilator. A control system continuously computes an ideal pressure-volume trajectory designed to cause the ventilator to deliver gas in the amount (tidal volume) and flow rate specified by the physician while allowing for different degrees of patient effort. Although this system permits the patient to over-ride physician-specified delivery pattern within an inhalation or over a brief period, the control system readjusts the terms in the equation, so that physician-determined criteria are ultimately met. The principle of control is, therefore, similar to volume-cycled methods, in that an increase in patient effort is met with a decrease in machine assist to return ventilator output to what the physician prescribes. The main difference from other volume-cycled methods is in the freedom the patient is accorded to transiently over-ride the prescriptions by the physician. This principle of operation is diametrically opposite to that executed by the method of the present invention. Thus, in the Stawitcke system, the physician sets targets for volume, flow and timing and the machine alters the various parameters in the control system equation in such a way as to meet physician requirements. By contrast, in the present invention, the proportionalities between pressure, on one hand, and volume and flow on the other hand are the parameters that are predetermined, while the patient is left entirely free to select volume, amount and pattern of flow, and timing of each breath.

It will be apparent from this discussion, that prior art patient ventilation systems provide ventilatory support to a patient in accordance with parameters which are determined mainly by a physician and not by the patient. Generally, the prior art has required some target flow rate, target pressure, target volume, and/or target frequency or inspiratory or expiratory time. Such requirements give rise to the various problems discussed above.

SUMMARY OF INVENTION

The present invention is directed to a quite different approach to ventilatory support from those of the prior art described above. In the present invention, the pressure delivered by the ventilator increases in direct proportion to patient effort, and the proportionality applies from breath to breath, as well as continuously throughout each inspiration. In effect, patient effort is amplified, thereby normalizing the relation between effort and ventilation, while leaving the patient entirely in control of all aspects of his breathing. In the present invention, the pressure delivered by the ventilator to the patient reflects the amplitude as well as the time pattern of patient effort (see FIG. 5). There is no target flow rate, no target pressure, no target volume, and no target frequency or inspiratory or expiratory time, as there is in the prior art. These parameters are determined solely by the pattern of patient effort and the ventilator simply amplifies the ventilatory consequences. The net effect of this approach is that the abnormal relation between effort and ventilatory consequences is restored towards normal, returning the patient's ability to alter ventilation and flow pattern, as dictated by his own varying needs, including the optimization of respiratory sensation. The ventilation procedure of the present invention may be termed proportional assist ventilation (PAV).

In the left-hand graph in FIG. 6, there is provided a summary of the relation between patient effort and pressure delivered by the ventilator with different ventilatory methods, while the right-hand graph shows the relation between patient effort and ventilatory consequences. With SIMV, PS, and APRV, there is a minimum ventilation in the absence of effort. Any influence the patient may have on his breathing is subject to the limitation imposed by disease (the slope of the line with SIMV, PS and APRV is similar to the of the disease line). With PAV, in contrast, the relation between effort and ventilatory consequences is normalized at different levels of effort.

In accordance with one aspect of the present invention, there is provided a novel type of lung ventilator apparatus which delivers PAV with a relatively simple electrically-powered operation. In the present invention, the gas pressure at the patient's airway is determined by the action of an electric motor acting on a piston reciprocating in a chamber in relation to any desired command input. The electrical motor moves the piston with a force proportional to the magnitude of the power applied to the motor. On-going rate of flow (V) and volume of flow (V) of gas moving from chamber to patient are monitored with electronic circuitry that permits the independent adjustment of the gain or amplifications of each of the two signals. The electronic circuitry provides electric power to the motor in proportion to the sum of the suitably amplified V and V signals. As is described in more detail below, this procedure causes the device to provide pressure in proporation to patient effort.

The difference between proportional assist ventilation and other modalities is that the patient has total control over his breathing pattern. In this modality, the apparatus works on the principle of positive feedback, namely the more volume and flow the patient takes, the more pressure the machine provides. The adjustable parameter is not a target pressure or a target volume, but a degree of assist (or proportionality) to the patient's breathing pattern. Thus, if the patient's respiratory system stiffness (elastance) is such that it requires 40 cmH$_2$O per liter of inflation, the machine may be adjusted to provide a specified amount of pressure/unit of inhaled air. If in this case, the proportionality is set to 20 cmH$_2$O/L, the patient has to do half the elastic work and the machine does the other half, and so on. There is no requirement that the patient take in a certain volume or reach a certain pressure. As soon as the patient decreases his own effort, air stops flowing in and the machine stops pumping.

Accordingly, in one aspect of the present invention, there is provided a method for providing breathing assistance in proportion to patient ongoing inspiratory effort, which comprises providing a free flow of gas from a gas delivery system to a patient in response to a pressure gradient generated by patient inspiratory effort; determining the rate and volume of flow of the gas to the patient; independently amplifying signals corresponding to the determined rate and volume of flow; and providing a pressure assist to the gas in proportion to the sum of the determined and amplified rate and volume of flow.

The present invention also provides apparatus for delivering proportional assist ventilation to a patient, comprising means for delivering a free flow of gas to the patient in response to patient inhalatory effort; means operatively connected to the gas delivery means for generating pressure in the free flow of gas in response to an electrical command signal; detection means for detecting the instantaneous volume and rate of gas flow to the patient and for generating a separate electrical signal corresponding in magnitude to each of the detected values; means for selectively applying amplification to each of the electrical signals; and means for generating the electrical command signal to the pressure generating means in proportion to the sum of the amplified electrical signals corresponding in magnitude to the instantaneous rate and volume of flow.

There are several advantages to this type of ventilation, in relation to the prior art ventilation devices and modalities.

The first advantage is one of comfort, in that the relation between machine and patient is not only synchronous, but entirely harmonious. There is no fighting between patient and machine, and, in fact, the ventilator becomes an extension of the patient's own muscles. Since with PAV pressure is only delivered if patient effort is present, and the pressure is proportional to patient effort throughout inspiration, the patient must contribute a fraction of the pressure used to expand the patient's chest. The ventilator needs to deliver less pressure for a given tidal volume, as compared with other devices. With other forms of ventilation, patient contribution cannot be relied upon and often patient contribution is antagonistic. The required peak airway pressure is higher with such devices than in the present invention. In preliminary studies, with the ventilation procedure of the invention, it was found that peak airway pressure with PAV was only one-third to one-half that with SIMV at the same level of ventilation. Since the required peak pressure is lower in the present invention, it is possible to ventilate some patients through a nose or face mask and avoid intubation altogether. Intubation, directly or indirectly, is one of the main causes of morbidity and mortality in ventilated patients.

Intrathoracic pressure remains negative during inspiration, as in normal subjects, thereby reducing the hemodynamic complications of artificial ventilation. The greater comfort, lack of fighting and possible avoidance of intubation greatly reduces the need for sedation or paralysis of patients, both of which impair the patient's defenses.

With PAV, the ventilator is simply an extension of the patient's own muscles and is, hence, subject to all the intrinsic control mechanisms that adjust ventilation to varying needs and protect against various injuries. Such control mechanisms can potentially be of considerable benefit. For example, the respiratory system is endowed with powerful reflexes to protect the lungs from overdistension. Overdistension would reflexly cause inhibition of inspiratory effort and recruitment of expiratory effort. Since the ventilator ceases its pressure when inspiratory effort is terminated, overdistension would reflexly cause the ventilator to cycle off. The risk of barotrauma is reduced. Furthermore, a patient's metabolic needs may vary greatly from time to time as a result of movement, shivering or temperature changes. Normally, the respiratory control changes inspiratory effort so that ventilation matches metabolic demands. With PAV, such adjustments in inspiratory effort would be met by concordant changes in machine assist. This effect tends to control arterial blood gas tensions within narrow limits. Furthermore, the patient would not fluctuate from periods of overassist to underassist, and hence distress, as his metabolic demands change.

With the present invention, there is less likelihood of inspiratory muscle disuse because a minimum level of inspiratory muscle activity must be present with the PAV modality. If PAV is used throughout the illness, there would be no period in which the central control mechanisms are inactive (apnea). Central respiratory dysfunction is common in the weaning period and may be due, in part, to protracted inactivity of the respiratory centres produced by machine settings that promote apnea with other modalities of ventilatory support. The lesser likelihood of central and peripheral muscle dysfunction facilitates weaning.

An improved efficiency of negative pressure ventilation is achieved. The ability of negative pressure devices to reduce intrathoracic pressure is limited, making them quite ineffective in patients with severe mechanical abnormalities (e.g. chronic obstructive pulmonary disease [COPD] or pulmonary fibrosis). Furthermore, the lack of harmony between pump pressure and upper airway dilator muscle activity promotes airway collapse. If the negative pressure applied to a body surface is harmonized with patient's own inspiratory effort, upper airway narrowing is decreased and the combined pump and patient generated pressure may be adequate for ventilation. These two factors may make it possible to ventilate patients with severe lung disease during sleep using the present invention. At present, cuirass ventilation in these patients (e.g. COPD) is feasible only during wakefulness.

An essential and distinguishing feature of the procedure of the present invention is that the pressure generated by the ventilator follows the exchange of gas from machine to patient as opposed to leading or causing it, as in conventional devices. Flow and volume must first be altered before the ventilator alters its pressure output.

Although the ventilating apparatus of the invention was designed specifically for the purpose of delivering this proportional assist mode, the design principles used to accomplish this end also make it possible to use the machine, with very minor electronic additions, to deliver pressure in proportion to any desired input. This extreme versatility permits adaptations to fit future needs with minimal modification.

GENERAL DESCRIPTION OF INVENTION

Figure 1:
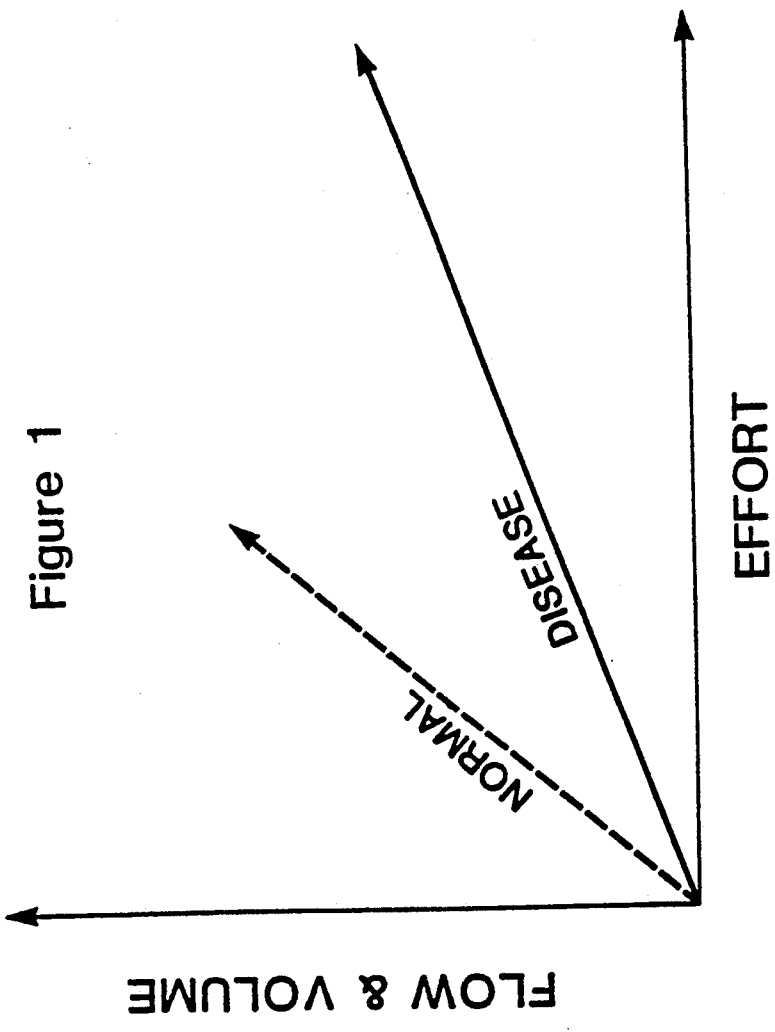
FIG. 1 is a graphical representation of patient effort and respiratory flow and volume.
Figure 2:
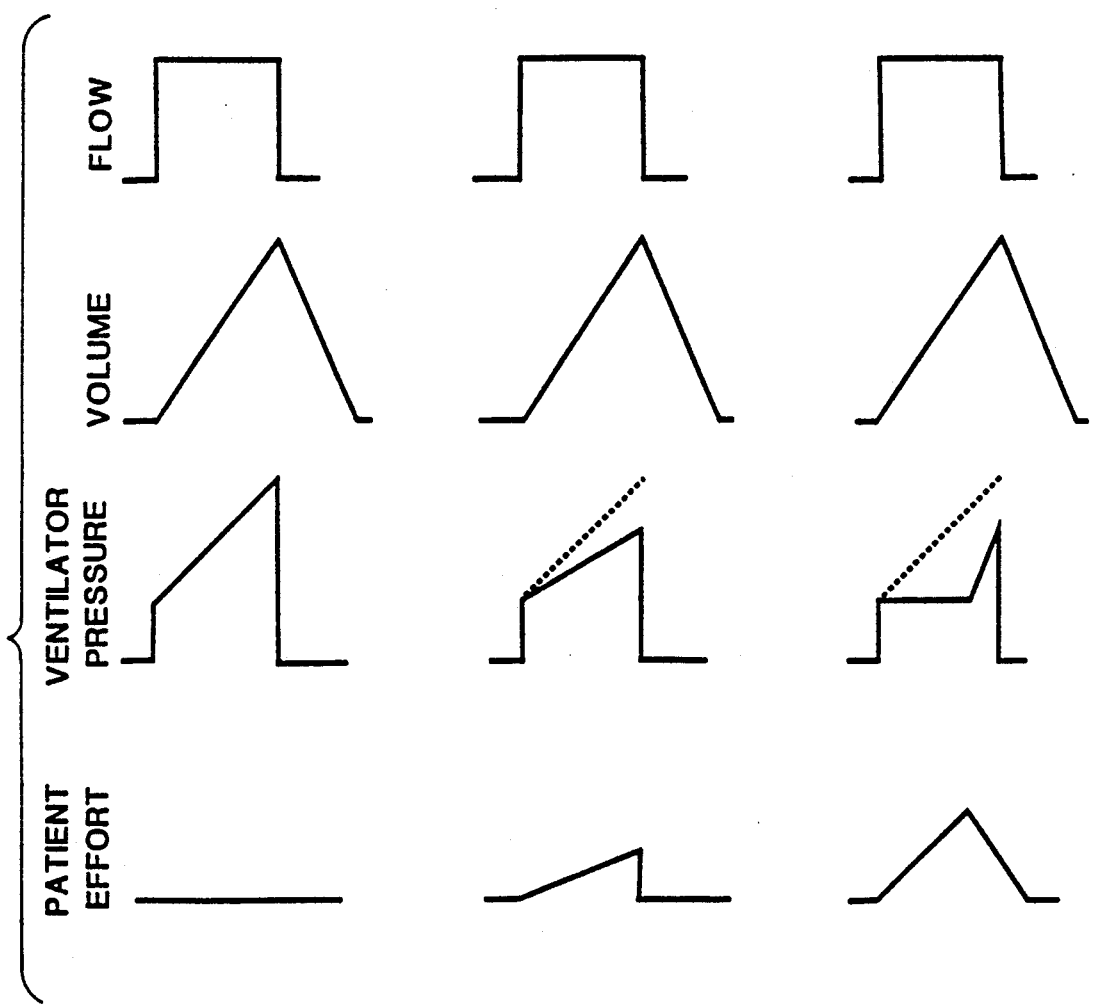
FIG. 2 is a graphical representative of volume cycled ventilation (VCV) according to one prior art procedure.
Figure 3:
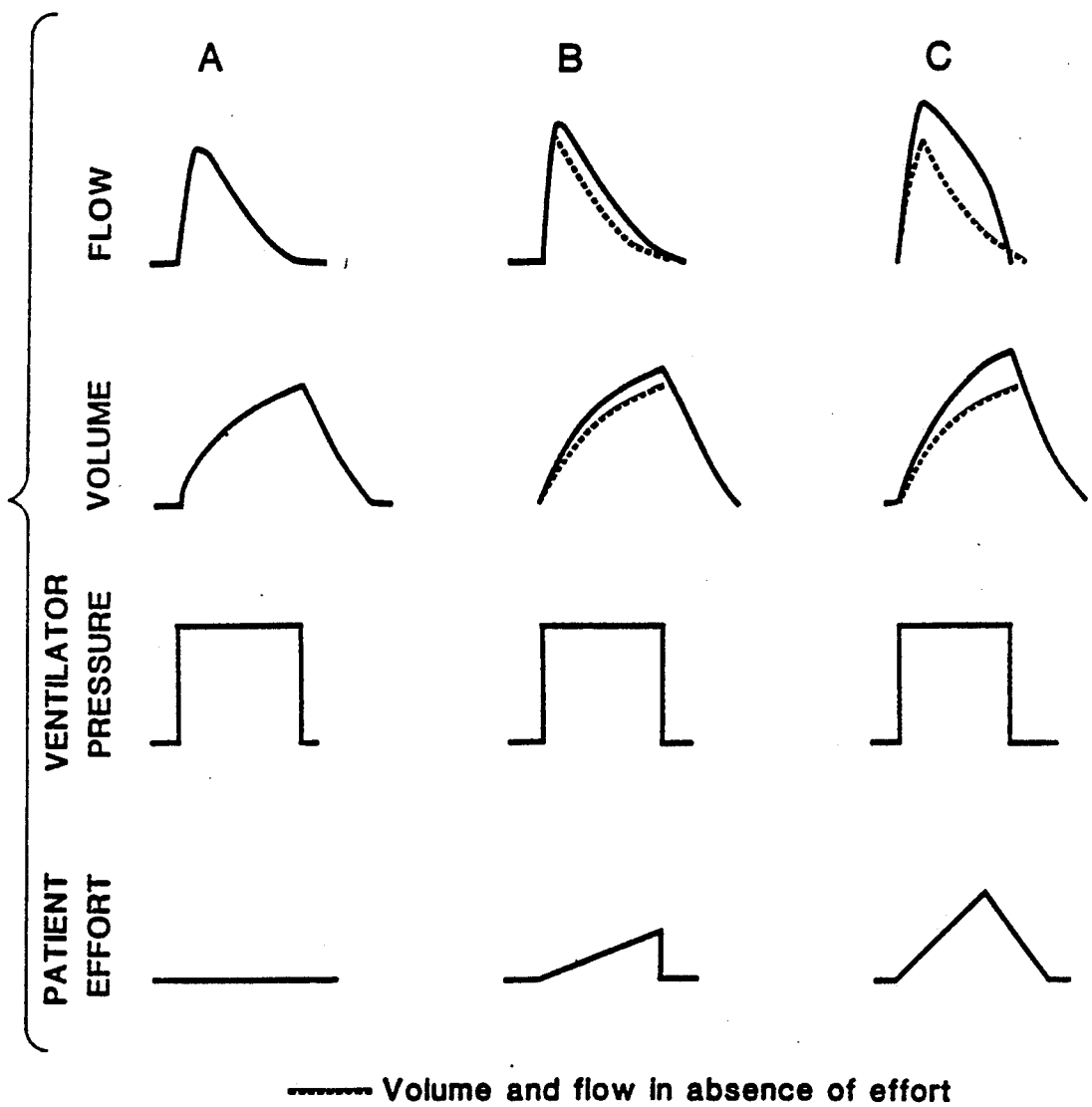
FIG. 3 is a graphical representation of pressure support ventilation (PSV), according to another prior art procedure.
Figure 4:
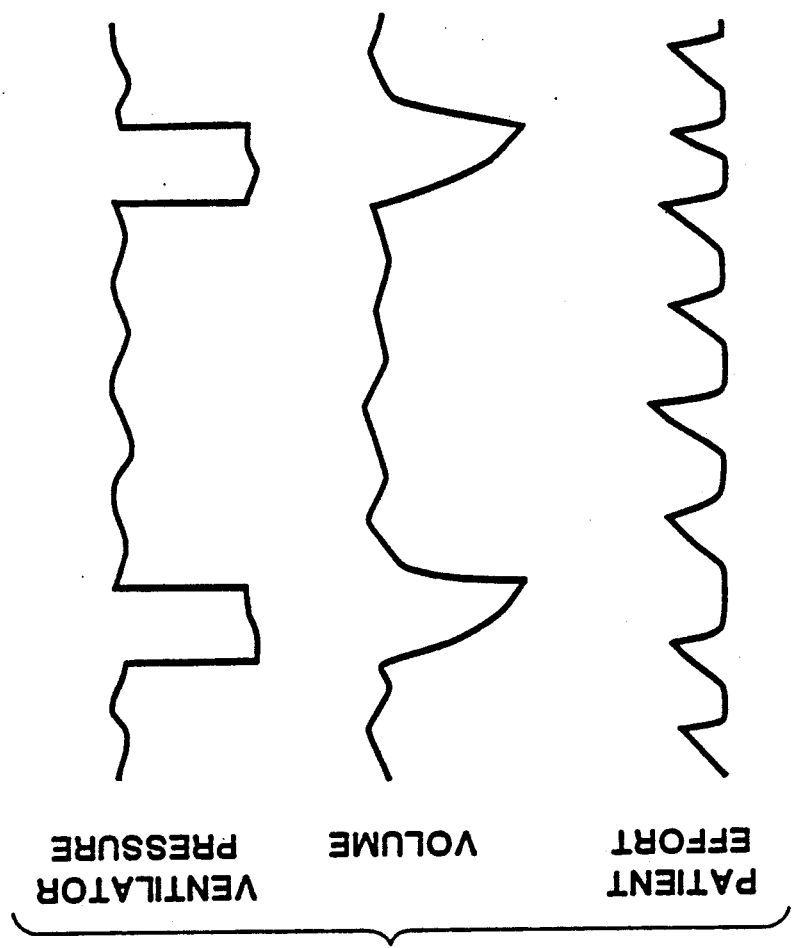
FIG. 4 is a graphical representative of airway pressure release ventilation (APRV) according to a further prior art procedure.
Figure 5:
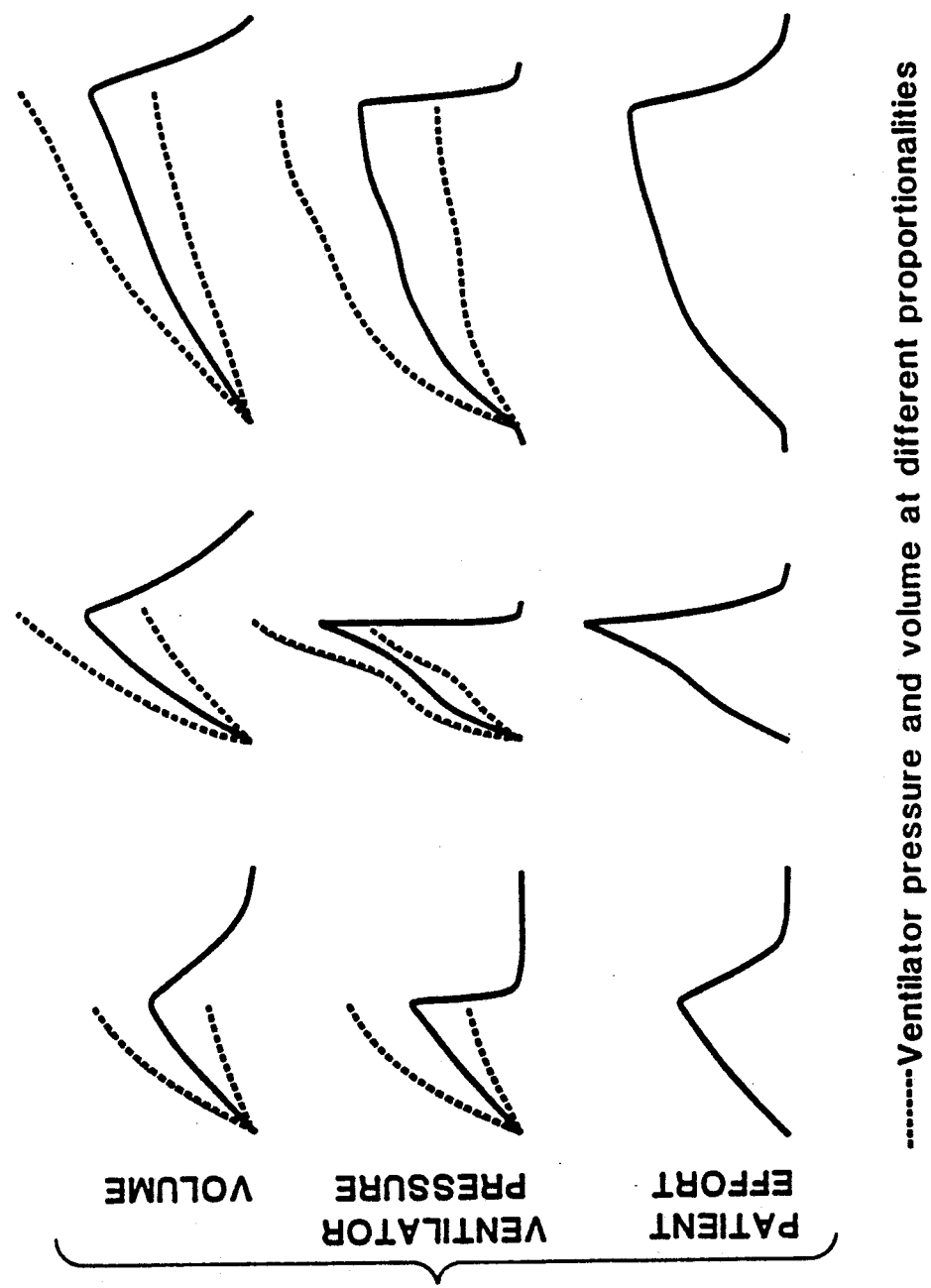
FIG. 5 is a graphical representative of proportional assist ventilation (PAV) according to the present invention.
Figure 6:
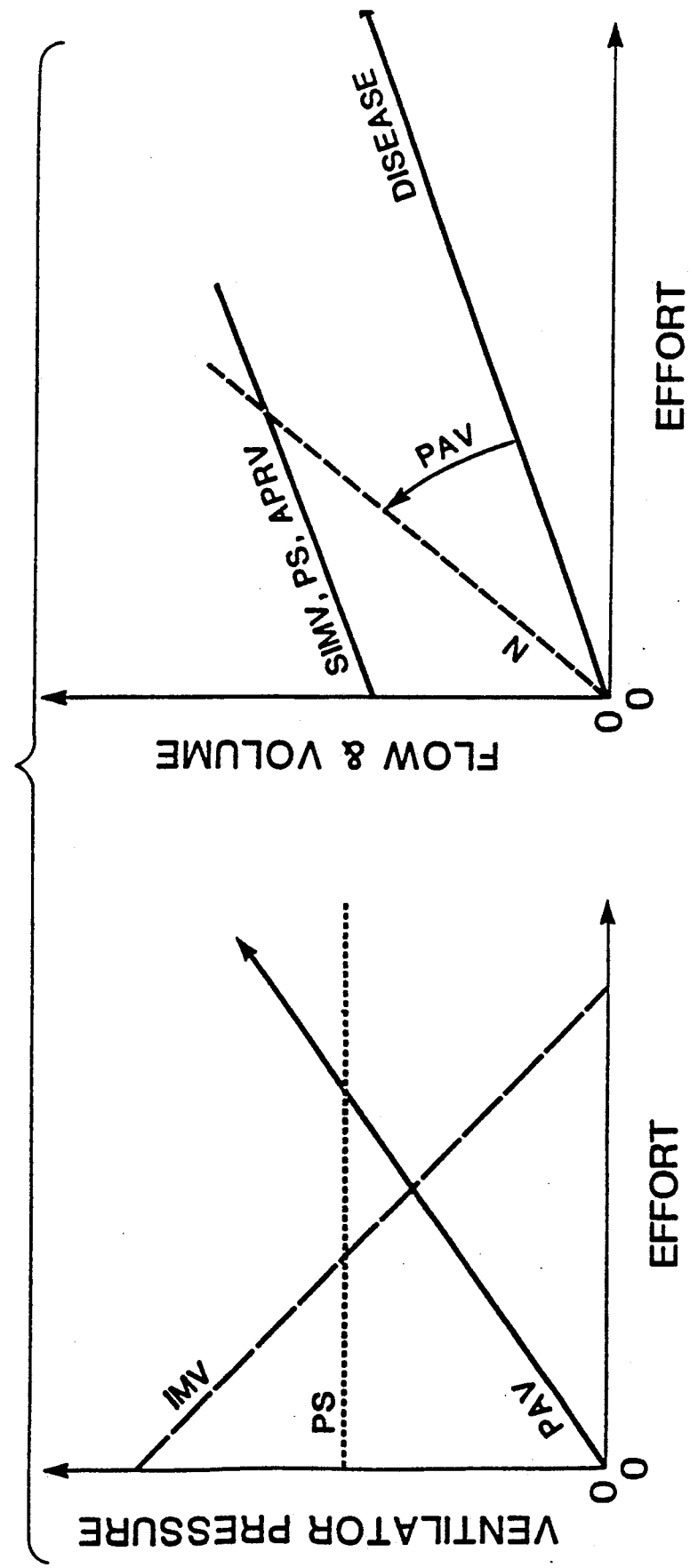
FIG. 6 is a graphical representative comparing proportional assist ventilation (PAV) in accordance with the present invention with prior art procedures.

In the present invention, patient effort is detected and responded to. Inspiratory effort can be defined as the degree of inspiratory muscle activation (Ei) relative to the maximal possible activation ($E_{max}$). Inspiratory activity results in generation of inspiratory pressure ($P_{mus}i$) according to the relationship:

$$[i.e.\ E_{max}]P_{mus}i = fEi/E_{max}$$

where f is the function that governs the conversion of activity to pressure. This function is primarily influenced by muscle strength, lung volume (V) and inspiratory flow (V̇) (see Younes et al, A model for the relation between respiratory neural and mechanical outputs. I.Theory, J.Appl. Physiol 51:963-978, 1981, incorporated herein by reference). Since maximal inspiratory pressure is not affected by volume in the resting tidal volume range and flow at resting levels is associated with very small velocities of muscle shortening relative to the maximal possible velocity (Younes et al, supra), the funcction that governs the relation between effort and $P_{mus}$ is primarily affected by muscle strength under resting levels of ventilation. This is very frequently abnormal in patients requiring ventilatory support because of primary neuromuscular disease, secondary to nutritional or metabolic derangements, or as a consequence of hyperinflation as in the case in patients with severe asthma or chronic obstructure pulmonary disease (COPD). Under these conditions, a given effort results in less than normal pressure and hence less expansion.

At any instant during the breath, the pressure applied to the respiratory system ($P_{appl}$) is dissipated against the elastic and resistive elements of the respiratory system, since inertial losses are negligible at resting levels of ventilation. Thus:

$$P_{appl} = P_{el} + P_{res}$$

where $P_{el}$ is a function of lung volume above passive Functional Residual Capacity (FRC) ($P_{el}=fv$), as dictated by the pressure-volume relation of the respiratory system, and $P_{res}$ is a function of flow, as dictated by the pressure-flow relation of the respiratory system. Although both functions may be complex and non-linear, linear functions are used in this discussion for convenience. Thus:

$$P_{appl} = V \cdot E_{rs} + \dot{V} \cdot R_{rs}$$

where V is the volume above ERC, $E_{rs}$ is the elastance of the respiratory system in the linear range (in cmH$_2$O/L), V̇ is the flow rate and $R_{rs}$ is respiratory system (including ventilating apparatus) resistance (in cmH$_2$O/L/sec).

During spontaneous breathing, the only source of $P_{appl}$ is pressure generated by the respiratory muscles ($P_{mus}$). In patients attached to a ventilator, applied pressure is the sum of patient generated pressure and machine generated pressure ($P_{vent}$). The latter may take the form of positive pressure at the airway or negative pressure at a body surface (e.g. by tank or cuirass).

During supported ventilation, it follows that the instantaneous relation between the opposing forces is determined by the relationship:

$$P_{mus} + P_{vent} = V \cdot E_{rs} + \dot{V} \cdot R_{rs} \qquad (1)$$

or $$P_{mus} = V \cdot E_{rs} + \dot{V} \cdot R_{rs} - P_{vent} \qquad (2)$$

Since V,V̇ and $P_{vent}$ can be continuously measured and $E_{rs}$ and $R_{rs}$ can be measured or estimated, $P_{mus}$ can be computed continuously, by any convenient computing device, from the measured values, and the ventilator device made to change pressure in proportion to the instantaneous $P_{mus}$.

$$P_{vent} = A \cdot P_{mus}$$

where A is the proportionality between $P_{vent}$ and $P_{mus}$ in cmH$_2$O/cmH$_2$O.

A simpler and more versatile approach is to design the ventilator such that it delivers pressure according to the following equation:

$$P_{vent} = K_1 V + K_2 \dot{V} \qquad (3)$$

where $K_1$ is a gain factor applied to the volume signal (in cmH$_2$O/L) and $K_2$ is a gain factor applied to the flow signal (in cmH$_2$O/L/sec). Although constants are used in this analysis, non-linear functions can be used where appropriate.

If A is the desired proportionality with $P_{mus}$ and $P_{mus}$ is given by equation (2) above, it follows that:

$$P_{vent} = A \cdot V \cdot E_{rs} + A \cdot \dot{V} \cdot R_{rs} - A \cdot P_{vent}$$

so that $$P_{vent}(1+A) = A \cdot E_{rs} \cdot V + A \cdot R_{rs} \cdot \dot{V}$$

or $$P_{vent} = [A/(1+A)]E_{rs} V + [A/(1+A)]R_{rs} \dot{V}$$

The latter equation has the same form as equation (3) above, where $K_1$ is a fraction (ie $A/(1+A)$) of respiratory elastance and $K_2$ is the same fraction of respiratory resistance. Accordingly, $P_{vent}$ can be made proportional to $P_{mus}$ without actually having to calculate $P_{mus}$ according to equation (2). Hence, if it is desired to produce a $P_{vent}$ which is three times as much as $P_{mus}$ (A=3), $K_1$ is set to be 0.75 $E_{rs}$ and $K_2$ is set to be 0.75 $R_{rs}$. It follows that either equation (2) or equation (3) can be used to control $P_{vent}$. However, the use of equation (3) is advantageous, for the following reasons.

With equation (2), $P_{vent}$ is used to derive the command signal to the pressure generating mechanism, while being, itself, the controlled variable. Particularly in view of the inevitable lag between command signal and $P_{vent}$, this situation promotes oscillations which require elaborate filtration to avoid.

Figure 11:
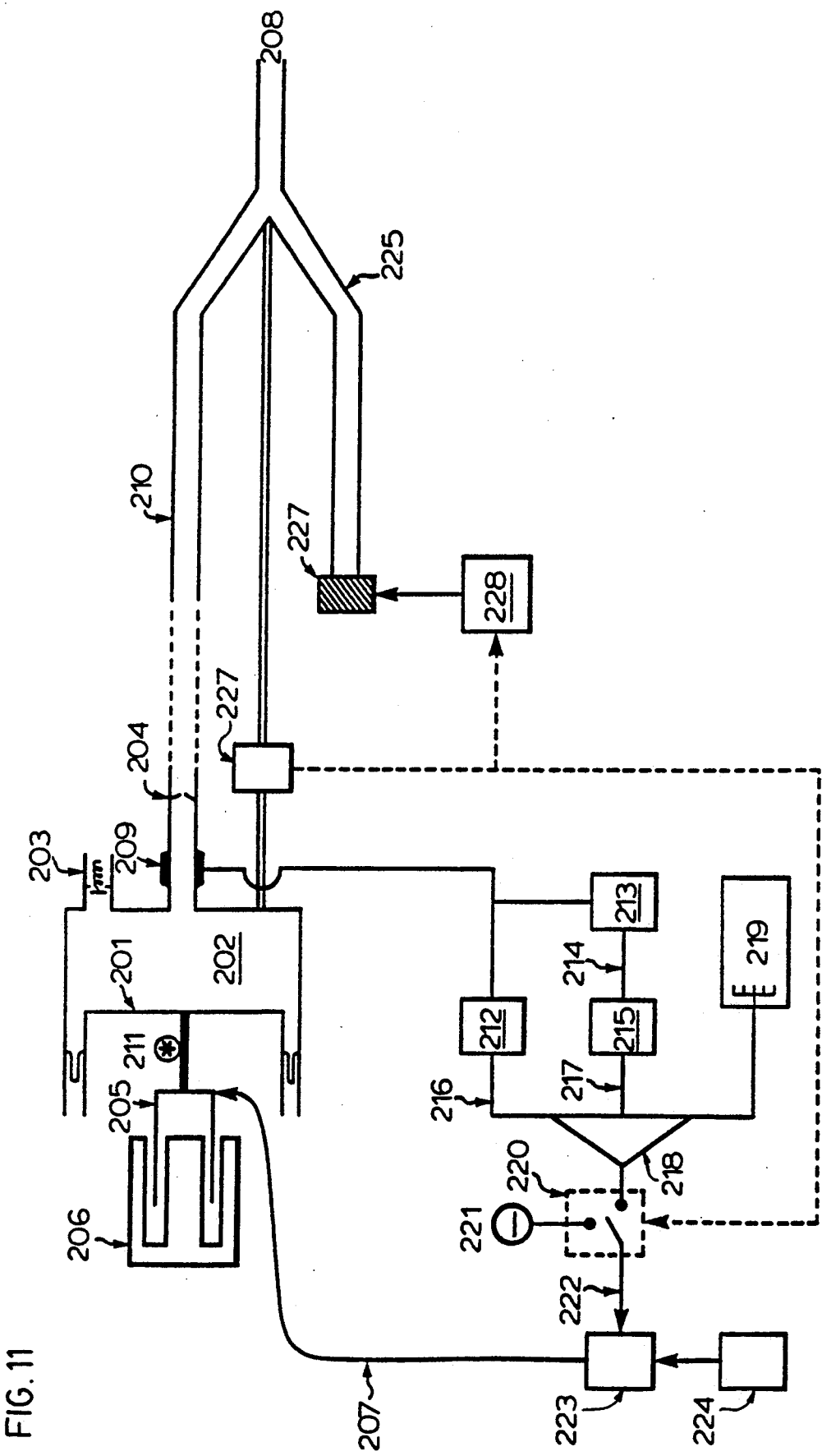
FIG. 11 is a schematic representative of a lung ventilator device for effecting proportional assist ventilation in accordance with another embodiment of the invention.

With equation (3), the use of individually adjustable gain factors for flow and volume permits unequal unloading of the resistive and elastic properties, which may have advantages in particular clinical situations. In addition, in many cases measurement of $E_{rs}$ and $R_{rs}$ are difficult to obtain or are unreliable, but with the use of equation (3), the gain factors for V̇ and V can be separately adjusted to patient comfort, thereby obviating the necessity of having to know $E_{rs}$ and $R_{rs}$. An example of a system which operates in accordance with this principle is shown in FIG. 11 and described below.

An essential and distinguishing feature of proportional assist ventilation (PAV) according to the invention, is that the pressure generated by the ventilator follows the exchange of gas from machine to patient, as opposed to leading or causing it. Flow and volume must first be altered before the ventilator alters its pressure output. Any device which delivers PAV to a patient, therefore, must permit free flow of air from the device to the patient in response to changes in pressure at the patient's end and this requirement is most readily exemplified by breathing from an easily-movable bellows.

Since, at any instant, the elastic and resistive pressure losses (right side of equation 1) are balanced by the sum of $P_{mus}$ and $P_{vent}$, any increase in $P_{mus}$ causes a change in total applied pressure and a corresponding change in flow and volume. The device then responds by changing its pressure, thereby causing a greater change in flow and volume.

A system that operates according to this sequence displays positive feedback. On its own, such a system is inherently unstable and tends to "run-away", since, as some air leaves the system, it generates pressure which causes more air to leave, causing the system to generate even more pressure, and so on. When attached to a patient, however, the positive feedback inherent to the ventilator is counteracted by the negative feedback provided by the mechanical properties of the patient, namely elastance and resistance.

Figure 7:
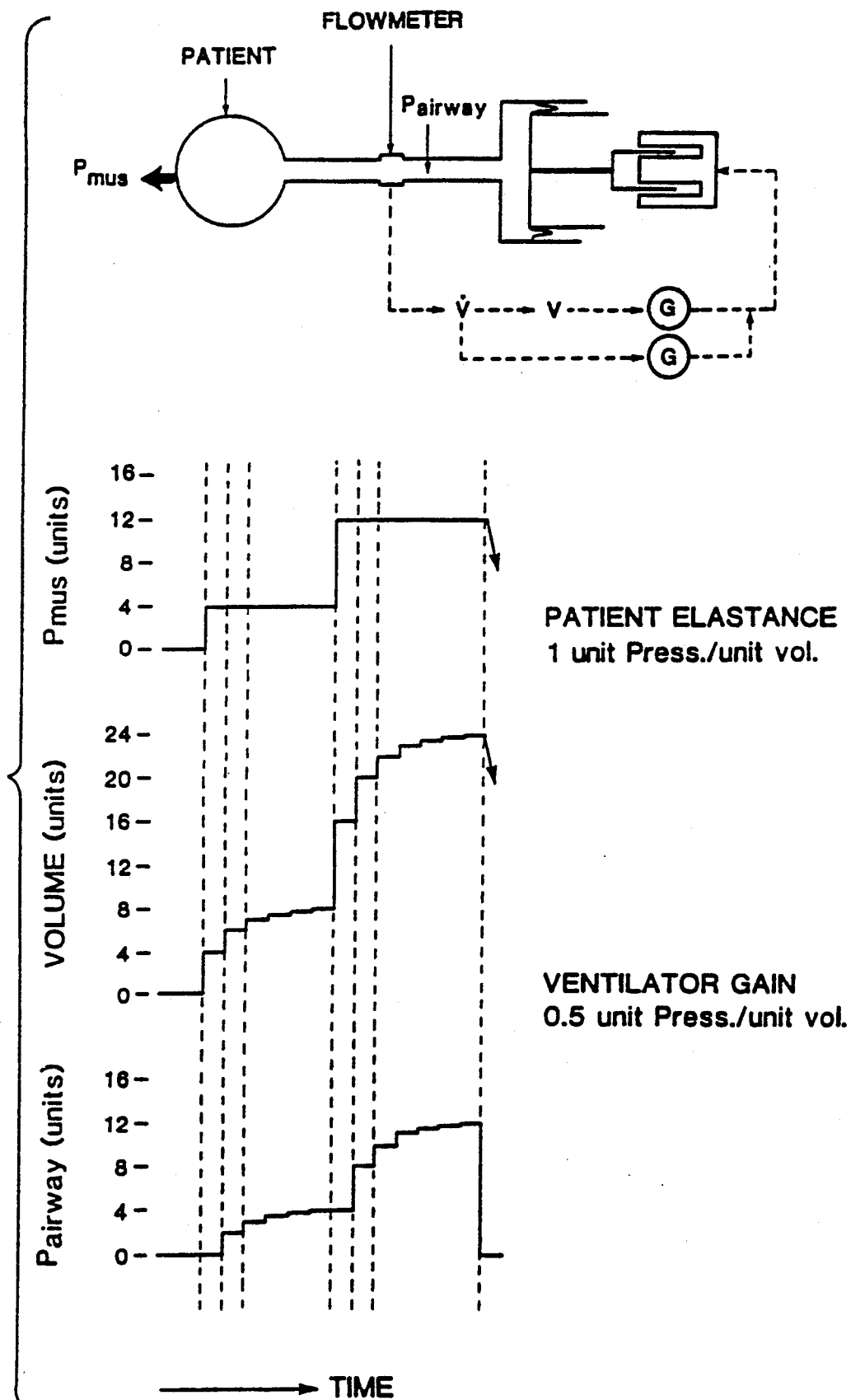
FIG. 7 shows a schematic of a device for providing proportional assist ventilation and a graphical representative of ventilator gain and patient elastance.

FIG. 7 schematically illustrates how the interaction between a PAV system and a patient tends to eliminate the potential for "run-away" and causes the system to simply amplify the ventilatory consequences of patient effort. The upper portion of FIG. 7 illustrates a simple design which satisfies the criteria of a PAV delivery system. The patient is attached to a freely-moving piston. Movement of air from the piston to patient is sensed by a flowmeter, resulting in flow and volume signals. The latter signals as measurements of the instantaneous rate and instantaneous volume of flow of ga are used to activate a motor which applies force to the back of the piston in proportion to the flow and volume signals. Separate gain controls determine the proportionalities between flow and volume on the one hand and the force exerted, namely resulting pressure, on the other hand. Such gain volumes are analogous to the terms $K_1$ and $K_2$ in equation (3).

To facilitate description of the interaction between the patient and a PAV system, the hypothetical case will be considered where all changes ($P_{mus}$ and $P_{vent}$) take place in discrete sequential steps, illustrated by the lower three graphs in FIG. 7, and all generated pressure is applied against the elastance of the respiratory system (i.e. the resistance is zero). Patient elastance is expressed in arbitrary units and is assigned a value of one (i.e. 1 unit pressure/unit volume).

Before the onset of inspiration, i.e. $P_{mus}$=zero, the airway pressure and volume are stable, reflecting the level of positive expiratory pressure (zero in the illustrated case). Assume the patient makes a step change in $P_{mus}$ of 4 units. According to patient elastance, four units of volume move from ventilator to patient. The airway pressure is still zero, as seen by the interval between the first pair of vertical lines. The transfer of gas (volume and flow), however, is sensed and causes the pressure in the system (i.e. $P_{aw}$) to increase according to the volume signal and the chosen gain factor. Assuming the gain factor is set at 0.5 units of pressure/unit of volume, the ventilator will increase $P_{aw}$ by 2 units of pressure in response to the initial four units of volume, so that the total pressure ($P_{appl}=P_{mus}+P_{aw}$) then has increased to six units, thereby causing two more units of volume to be transferred. This increased volume, in turn, is sensed and, according to the gain factor; causes $P_{vent}$ to rise an additional one unit, which itself results in the transfer of one more unit of volume, and so on.

It can be seen that, because the gain factor is less than the elastance of the patient, the magnitude of the steps decreases progressively and, accordingly, there is no tendency to "run-away". In fact, if $P_{mus}$ remains constant, the volume rises to an asymptote. This effect can be seen graphically in FIG. 7, the volume asymptote is twice the value produced by the patient in the absence of assist.

With a larger step change in $P_{mus}$, for example the second step in FIG. 7, the volume exchanged under the patient's own power is larger, and so is the response of the ventilator but, again, there is no tendency to run-away, and the volume exchanged in this second step bears the same proportionality to $P_{mus}$ as the smaller first step.

Since the elastic recoil at any instant is sustained jointly by patient and ventilator, if the patient decreases his contribution, as signified by the arrow in FIG. 7, the pressure applied to the respiratory system, namely $P_{mus}+P_{vent}$, is no longer sufficient to sustain the system's elastic recoil. As in the case of spontaneous breathing, when $P_{mus}$ decreases at the end of inspiration, a positive gradient develops from alveoli to airway and exhalation begins.

The extent of amplification of the elastic component of $P_{mus}$ is a function of the gain on the ventilator volume signal ($K_1$) relative to the patients own elastance ($E_{rs}$). Since the total elastic pressure ($V.E_{rs}$) is balanced in part by the elastic component of $P_{mus}$ ($P_{mus}$ (el)) and in part by the elastic assist of the ventilator ($V.K_1$), it follows that:

$$P_{mus}(el) = V \cdot E_{rs} - P_{vent}(el)$$
$$= V \cdot E_{rs} - V \cdot K_1$$
$$= V(E_{rs} - K_1)$$

The ratio of total elastic pressure applied, namely $V.E_{rs}$, to that developed by the patient ($P_{mus}$ (el)), which is the elastic amplification factor (F(el)), therefore, is given by the equation:

$$F(el) = V \cdot E_{rs}/V[E_{rs}-K_1] = E_{rs}/[E_{rs}-K_1]$$

Hence, if $K_1$ is $\frac{1}{2} E_{rs}$, as in the example of FIG. 7, then the amplification factor is 2. For $K_1 = 0.75 E_{rs}$, the amplification factor is 4, and so on. Where $K_1$ equals or exceeds $E_{rs}$, amplification would be infinite and a run-away situation would result. However, since $E_{rs}$ increases progressively as long as volume increases, a run-away situation produced by the gain factor accidentally being higher than $E_{rs}$ near functional residual capacity, would soon be aborted as lung volume increases and $E_{rs}$ increases.

The example shown in FIG. 7 is intended as an oversimplification to explain the principles involved in the present invention. For example, the resistance is never zero and part of $P_{mus}$ is expended against the resistance elements of the system (patient plus equipment). However, similar analysis and consideration can be made to the resistance component of $P_{mus}$, i.e. $P_{mus}(res)$. At any instant, the total pressure used to offset the flow-related pressure gradient is given by V. R, where R is the total resistance for airflow from ventilator to chest wall and includes equipment resistance. This pressure is provided in part by the ventilator ($V.K_2$) and in part by the resistance component of $P_{mus}$ ($P_{mus}(res)$). Using a similar analysis as that for elastic pressure, it can be shown that the amplification of the resistance component of $P_{mus}$ (F(res)) is a function of the flow gain on the ventilator ($K_2$) relative to the total resistance (R), according to the relationship:

$$F(res) = R/[R - K2]$$

Because volume rises gradually during inspiration whereas flow peaks early on and declines later in inspiration, the partition of $P_{mus}$ between elastic and resistance components varies greatly with inspiratory time. $P_{mus}$ (res) contributes the largest fraction of $P_{mus}$ early in inspiration with this fraction declining to nearly zero by the end of inspiration. The correlation between instantaneous flow, and hence $P_{mus}$ (res), and instantaneous effort, i.e. total $P_{mus}$, is quite poor and, in fact, negative later in inspiration. An assist related to flow only, therefore, would amplify effort early in inspiration, where effort is small, while leaving the muscles essentially unsupported late in inspiration, where effort is greatest.

Similarly, because $P_{mus}(el)$ constitutes a different fraction of total $P_{mus}$ at different times of inspiration, volume is not a perfect correlate of effort, although, because both $P_{mus}$ and volume rise during inspiration, the correlation is better than in the case of flow. Nonetheless, assist proportional to volume only would provide $P_{mus}$ amplification primarily late in inspiration, but would leave the early part of inspiration essentially unsupported. This result would not be particularly adverse if resistance is normal since, in this case, the relation between effort and ventilatory consequences early in inspiration would be normal and not requiring support. However, since R is abnormal in all ventilated patients, at least because of the added resistance of the endotracheal tube and apparatus resistance, the failure of $P_{mus}$ amplification early in inspiration would leave the patient with a sense of loading which may lead to respiratory distress. The patient's own resistance also may be high, although the increase in inspiratory airway resistance even with very severe obstructive diseases is only modest and the main load is still primarily elastic, as dictated by dynamic hyperinflation.

Another consideration regarding the use of support in proportion to either flow or volume alone is the fact that amplification of one component of $P_{mus}$, namely $P_{mus}(el)$ or $P_{mus}(res)$, inevitably results in an increase in the contribution of the other, unsupported, component. Thus assist in proportion to flow will initially increase flow. Lung volume, and hence elastic component of $P_{mus}$, rises at a faster rate. The contribution of $P_{mus}$ (res), and hence the assist, must subsequently decline as a result.

It follows from this discussion that, in order to normalize the relation between effort and its ventilatory consequences, it is necessary to provide support to both flow and volume, according to equation (3) above. In this way, $P_{mus}$ is amplified regardless of how it is partitioned between elastic and resistive components.

The illustration shown in FIG. 7 also should not be interpreted as implying that the control should proceed in a sequential manner as illustrated. Analog control circuitry can function just as well. In both cases (digital and analog) the command signal to the pressure generator changes only subsequent to, and not in advance of, a change in flow and volume thereby rendering the ventilator subservient to the patient and not the opposite.

DESCRIPTION OF PREFERRED EMBODIMENTS

For the delivery of PAV, motor driven bellows is the preferred basic design, since the relation between command signal and pressure output is more direct, as opposed to gas powered ventilators where pressure can be varied only by controlling flow. The relation between flow and system pressure is extremely complex. Delicate servo control would be essential and this would tend to cause oscillations in the PAV modality, unless severe filtering is applied which considerably dampens the response, as described above.

Two embodiments, utilizing motor driven bellows, are described below. The first, more complex one (FIGS. 8 to 10), is recommended where the relation between power supplied to motor and pressure output is not intrinsically linear. This may arise because the properties of the mechanical components (bellows and motor) are such that a significant amount of the force generated by motor is dissipated in overcoming the inertia and resistance of the piston/motor. Since acceleration and flow vary greatly during inspiration, inertial and resistive force losses also would be highly variable, resulting in an unreliable intrinsic relation between force and pressure. Alternatively, nonlinearities between applied power and pressure output may arise if the motor operates in its non-linear range. In both cases, these non-linearities must be compensated for through servo-feedback where the power supplied to the motor is related to an error signal (difference between actual and desired pressure), as opposed to being related to the primary signal itself (sum of flow and volume in the case of PAV).

The second embodiment (FIG. 11) is suitable where the relation between power delivered to motor and pressure in the bellows is linear in the range of motion required for ventilation. This is achieved by mechanical design that minimizes inertial and resistive losses during movement of piston or bellows and by insuring that the motor operates in a linear range (i.e. fixed relation between power supply and force output) through the entire clinically-useful volume range of piston or bellows. The use of such mechanical design obviates the need for using pressure feedback and error signal to control the motor. As indicated earlier, the use of pressure feedback in the PAV modality destabilizes the device (because the desired pressure is not itself a fixed reference or function but is highly labile and influenced by the pressure in the system). Eliminating the pressure feedback from the command signal, therefore, results in a much more stable system. Filtering can be minimal with enhanced responsiveness of the device. The operation of such device then would be essentially errorless.

Figure 9:
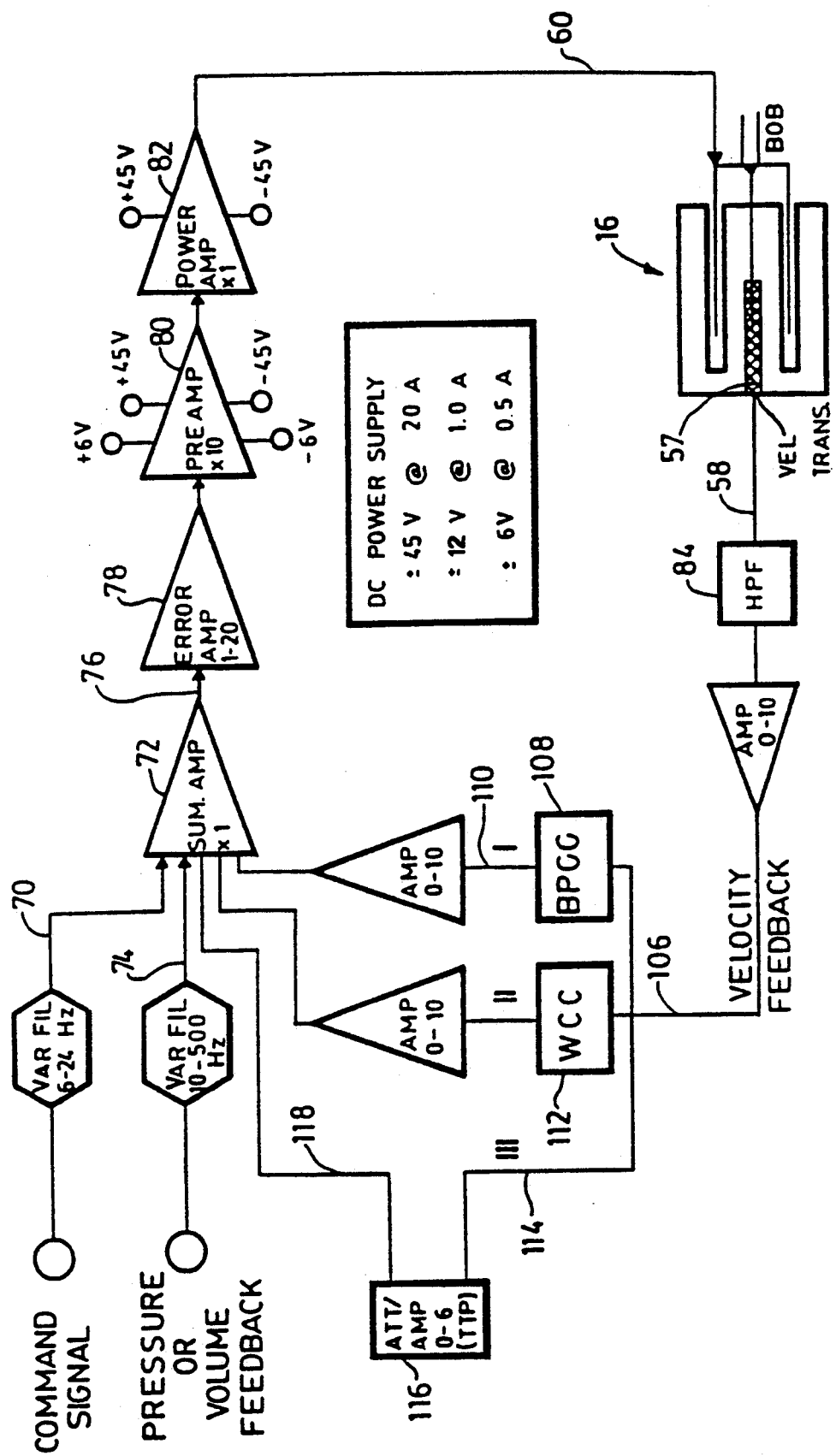
FIG. 9 is a schematic representation of the electronic circuitry used with the apparatus of FIG. 8.
Figure 10:
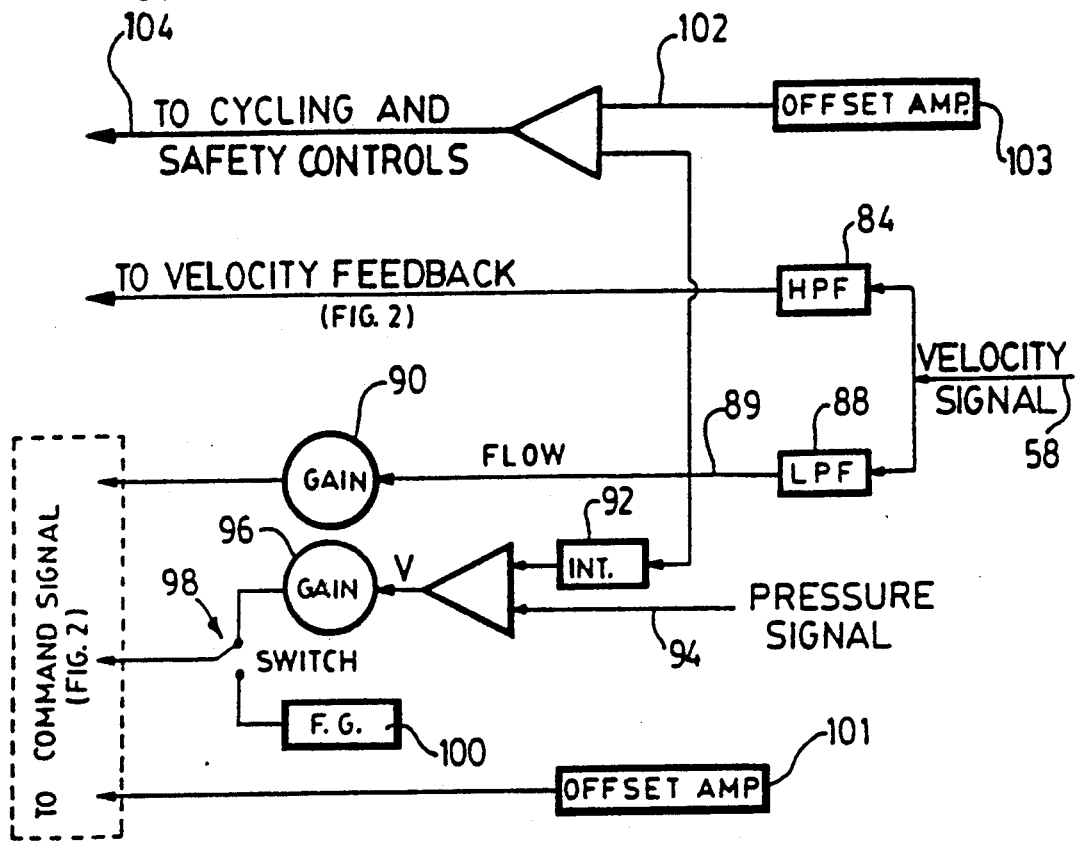
FIG. 10 is a schematic representation of the various command signals for the electronic circuitry of FIG. 9.
Figure 8:
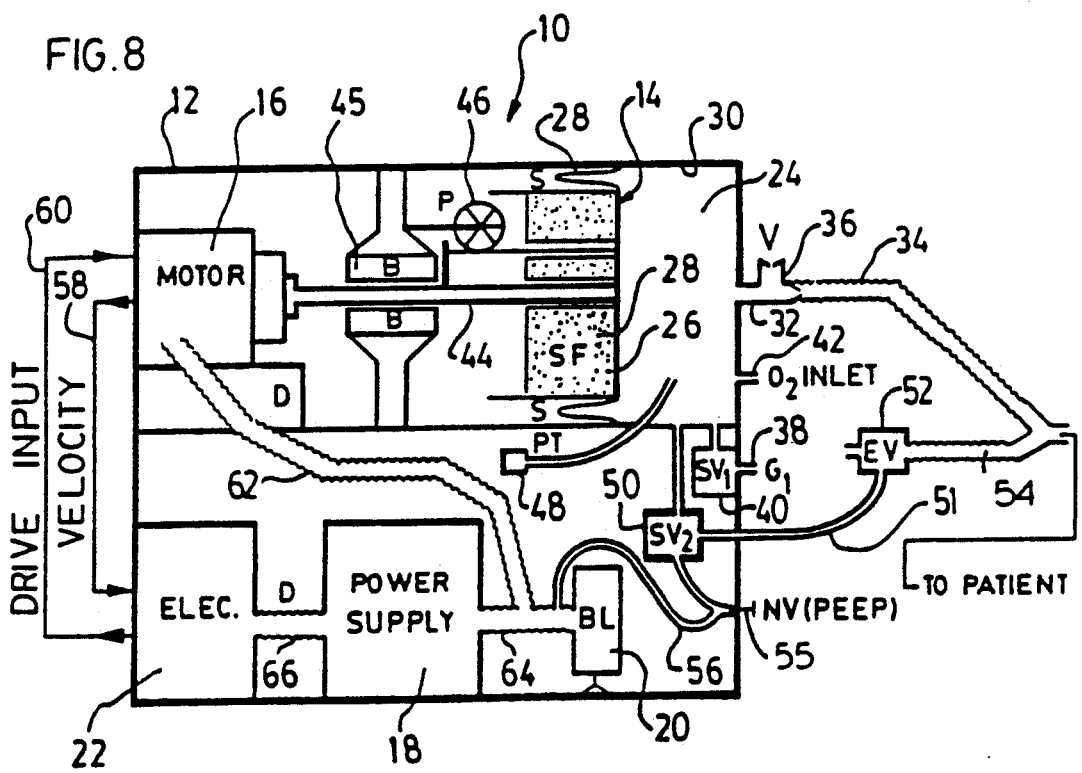
FIG. 8 is a schematic representation of a lung ventilator device provided in accordance with one embodiment of the invention.

Referring to FIGS. 8 to 10 the drawings, a lung ventilating apparatus 10 comprises a plurality of components housed in housing 12. The components located in the housing 12 comprise a rolling seal piston head 14 of low inertia and low resistance, a drive motor 16 for the piston 14, an electrical power supply 18 for the unit 10, and air blower 20 and electronic controls 22.

The piston head 14 is mounted for reciprocal movement in the housing 12 to provide a chamber 24 of variable volume depending on the position of the piston head 14. The cross-sectional area of the piston head 14 as well as the maximum distance of reciprocation determine the range of ventilation for which the unit 10 may be used.

For best patient response, the piston head 14 should move with little inertia and frictional resistance, so that the initial movement of the piston follows free flow of gas to the patient upon initial patient inhalation effort. For this purpose, a light plastic material may be employed as the material of construction, or, as illustrated, an aluminum sheel 26 with a foamed polymer reinforcement, such as, Styrofoam. Frictional resistance to piston movement may be decreased by using high quality bearings and low resistance seals, such as a rolling seal 28 between the piston head 14 and the interior chamber wall 30.

The chamber 24 is provided with an inlet/outlet opening 32 which is arranged to be joined by a flexible air pipe 34 to the airway of a patient. A one-way valve 36 communicates with the pipe 34, to allow ambient gas, usually air, to enter the piston chamber 24 through the inlet/outlet opening 32 during the exhalatory phase of the respiratory cycle, as described in more detail below.

The chamber 24 is illustrated as possessing an additional gas inlet 38 controlled by a solenoid valve 40 to permit the optional introduction of selected gas mixtures, if desired, to the chamber 24. The solenoid valve 40 is opened during expiration as the piston head 14 reciprocates to its baseline position. Alternatively, the oxygen content of the inspired gas may be enriched by admitting a continous flow of oxygen into the chamber 24 through an optional gas inlet 42.

The piston head 14 is mounted on a piston rod 44 for reciprocation of the piston head 14 for the purpose of alternatively decreasing and increasing the volume of the cylinder 24. The piston rod 46 is mounted in sliding relation to a suitable bearing 45. A position sensing device 46, in the form of a potentiometer, is mounted on the piston rod 44 to provide an electrical signal corresponding to the position of the piston head 14.

A pressure transducer 48 is operatively connected to the piston chamber 24 to determine the pressure in the chamber 24 which, in turn, determines the force output required by motor 16, as explained in more detail below.

The piston chamber 24 also is connected to a three-way solenoid valve 50. The solenoid valve 50 is connected via tube 51 to an expiratory valve 52 connected by flexible tubing 54 to the patient airway. During the inspiratory phase of operation of the piston 14, the solenoid valve 50 connects the chamber 24 to the expiratory valve 52, shutting it off. During the expiratory phase of operation of the piston 14, the solenoid valve 50 connects the expiratory valve 52 to a variable pressure in order to set the level of positive end-expiratory pressure (PEEP). The variable pressure is produced by controlling the resistance of a needle valve 55 mounted into the pipe 56 connecting the solenoid valve 50 to the blower 20.

The motor 16 is of the type which possesses a moving part, such as a shaft or coil, to exert a force in a forward (positive) or backward (negative) direction in proportion to the power applied to the motor 16. The maximum force requirement of the motor is determined by the area (A) of the piston head and the maximum pressure range (Pmax) for which the unit 10 is built. The equation to calculate the required force is:

$$F(kg) = \frac{Pmax \text{ (cm } H_2O) \times A \text{ (cm}^2)}{1000}$$

Hence, for example, for a piston of area 200 cm$^2$ and maximum pressure range 50 cm H$_2$O, the motor 16 should be able to generate up to 10 kg of force.

A velocity transducer 57 (FIG. 9) is mounted to the core of the motor 16 to generate a signal 58 proportional to the rate of motion of the piston head 14. This signal is used for a variety of purposes, as described below with respect to FIG. 9. The motor 16 is powered by a power line 60 from the electronic module 22 (see also FIG. 9).

While we found the above described mechanical design suitable, clearly any other motor/bellows design or configuration that satisfied the low inertia/low resistance requirement of this application would be suitable.

The electronic module 22 functions to provide the electrical signal drive input 60 to the motor 16 to cause the motor 16 to generate a drive force to the piston 14 of a pattern and magnitude that reproduces, as closely as possible, the desired pattern and magnitude of pressure to be delivered to the patient from the chamber 24. It is preferred to employ a fast-responding motor, so that a change in drive input results in an almost instantaneous change in drive force, thereby permitting almost unlimited patterns of pressure applications in response to patient inspiratory effort.

A large variety of electronic components may be used in the electronic circuitry in conjunction with the pressure generating device (i.e. the combination of motor 16, piston head 14 and power supply 18) to produce a corresponding variety of pressure patterns, as described further below.

The operation of the ventilating device 10 now is described in conjunction with the electronic circuitry shown schematically in FIG. 9 and the command signals shown schematically in FIG. 10.

The motor 16 responds to the instantaneous difference, after suitable amplification, between a desired output, being the command signal, and the actual output. As seen in FIG. 9, the desired output is inputted by line 70 to a summing amplifier 72 to which also is fed a feedback signal (corresponding to the actual state of affairs) by line 74.

To produce a signal that is proportional to the inspired volume, the inspired volume signal is connected to the command signal. The pressure in the piston chamber 24, as measured by the pressure transducer 48, is used as feedback. If the measured pressure in the chamber 24 is different from the one desired as determined by the summing amplifier 72, then an error signal is generated in line 76. The error signal, after suitable amplification by amplifiers 78, 80, then controls the output of a power amplifier 82 which provides the control signal in line 60 to the motor 16.

When the pressure in the piston chamber 24 is measured by the pressure transducer 48 as just described, the ventilator unit 10 can deliver pressure from the piston chamber 24 in proportion to inspired volume (as just described) or inspired flow rate (with the flow rate used as the command signal). For the PAV operation, the ventilator unit delivers pressure from the piston in response to a combination of the instantaneous inspired volume and inspired flow rate, and in accordance with the desired proportional assist.

This basis design also can be used to implement other methods of assist as per prior art methods. For example, if a sine wave or a ramp voltage is used as the command signal, the ventilator unit produces pressure in the corresponding manner. As a result of this versatility, it is possible to employ the unit 10 as a high frequency ventilator alone or in combination with volume and flow assist.

If inspired volume is used as a feedback, the unit also delivers pressure in a pattern which causes inspired volume to follow the pattern of the command signal, thereby functioning as a volume ventilator.

In the electronic circuitry 22, the summing amplifier 72 also receives feedback from the velocity transducer 57 by line 58. This additional feedback tends to prevent rapid changes in pressure which otherwise may trigger oscillations, as previously discussed with reference to equation (2). The output of the velocity transducer 57 reflects the motion of the piston as air moves into the subject as well as motion related to compression or decompression of gas in the system. The former component is a relatively slow event whereas the latter component incorporates high frequency components, which are desirable as feedback to prevent oscillations. For this reason, the signal in line 58 is passed through a high pass filter 84. The filter output in line 106 is used as a velocity feedback in three arms.

One arm of the net velocity signal in line 106 is passed through a bidirectional peak clipping circuit 108, which clips the signal above and below an adjustable level. The signal so produced in line 110 is amplified and passed to the summing amplifier 72.

A second arm of the net velocity signal in line 106 is passed through a window clipping circuit 112, which passes only that part of the signal above or below an adjustable level and is designed to abort massive oscillations in the event of failure of other feedback. The level above or below which net velocity signal is passed is adjusted to be above the signal level associated with response to the control signal.

The third arm, in line 114, containing the entire net velocity signal, is passed through an adjustable attenuator with the resulting signal passing by line 118 to the summing amplifier 72. With the two clipping circuits 108 and 112 in place, the gain on the main velocity signal in line 114 need only be small.

Generally, switches permit the operator to select the function or combination of functions to be channeled to the summing amplifier 72 and variable gain controls permit selection of the magnitude of the assist. The various functions available for the illustrated embodiment are shown schematically in FIG. 10 and will now be described:

(a) Inspired flow: When the high frequency components of the output of the velocity transducer 57 in line 58 are filtered out, the remaining signal agrees very well with flow measured independently at the airway 34 and hence represents, at any given time, the instantaneous gas flow rate. Accordingly, the velocity flow signal in line 58 is passed through a low pass filter 88 and the resulting signal 89 is used as a command signal in line 70 for the ventilator unit 10 to produce pressure in proportion to inspired flow (i.e. resistive assist). A gain control 90 permits the selection of the magnitude of the assist by suitable amplification of the electrical signal corresponding in magnitude to the detected instantaneous inspired flow rate. Clearly, other conventional methods of measuring the rate of flow from chamber to patient would be equally suitable.

(b) Inspired volume: The signal related to inspired flow (line 89) may be integrated in integrator 92 to provide a signal corresponding to inspired volume and hence represents, at any given time, the instantaneous gas flow volume. When the resulting signal is routed to the summing amplifier 72 by line 70, the ventilator unit 10 develops pressure in proportion to inspired volume. The magnitude of the assist obtained again may be controlled by a gain device 96 by suitable amplification of the electrical signal corresponding in magnitude to the detected instantaneous inspired flow volume.

(c) Ramp generator: This mode of operation permits the ventilator unit 10 to function independent of patient effort and provides a controlled ventilation. This function can be activated by the operator by throwing switch 98 to bring the function generator 100 into the circuit. Alternatively, provision may be made for the ramp generator to be routed automatically to the summing amplifier 72 in the event of the failure of the patient to breathe spontaneously for a specified period of time (not shown).

(d) D.C. output: An adjustable DC output provided by an offset amplifier 101 also is routed to the summing amplifier 72, to result in the generation of continuous pressure.

The electronic circuitry 22 also includes cycling controls (not shown) to take into account that air is exchanged between patient and ventilator unit 10 only during the inspiration phase of the respiratory cycle and it is necessary to reset various controls in the "off" phase in preparation for the next cycle. These controls also effect closure of the expiratory valve 52 during the pumping phase.

During inspiration, air moves from the piston chamber 24 to the patient via tube 34. During expiration, air escapes by the expiratory valve 52 while the one-way valve 36 prevents expired air from re-entering the chamber 24.

At the commencement of inspiration, the piston head 14 begins to move forward in the chamber 24, either as a result of the patient pulling in (assist mode) or as a result of the piston pushing (in response to a ramp command in the controlled mode). This forward motion then generates a flow signal which, when it exceeds a predetermined level, causes the expiratory valve 52 to close to ensure that pressure is conveyed to the patient. This result is achieved by summing the flow signal in line 89 with a DC offset voltage in line 102 from offset amplifier 103 and passing the summed signal in line 104 through a zero crossing detection circuit.

The level of the offset voltage 102 may be varied and usually is kept slightly above zero. Once the flow exceeds this minimal level, a square voltage output is generated which activates valve 50, thereby connecting the chamber 24 to the valve 52 and closing the latter. Flow then continues into the patient as long as patient effort plus pressure output by the ventilator unit 10 exceed the elastic recoil of the respiratory system.

When patient effort declines at the end of the patient's spontaneous inspiration, inspiratory flow ceases.

As the flow signal crosses the offset level on its return to zero at the end of the inspiratory cycle, the valve 50 is inactivated, so releasing the pressure in the expiratory valve 52 and allowing the patient to exhale.

At the same time, a negative voltage is gated to the summing amplifier 72, which causes the piston head 14 to pull back allowing air to enter the chamber 24 through the one-way valve 36, if air is the desired gas. If desired, the solenoid valve 40 may be opened at the same time to permit pressurized gas of a specific composition to be admitted. The piston head 14 retracts until the piston position, as indicated by the output of the potentiometer 46, reaches a preset level.

When this condition is reached, the negative voltage to the summing amplifier 72 is interrupted and the solenoid valve 40 is closed. The active command signal is the output of the offset amplifier. The pressure in the piston chamber 24 remains at this level throughout the remainder of the expiratory phase and until the beginning of the next inspiratory phase. The output of the offset amplifier is normally set just below its PEEP level, so that the patient need only exert minimal effort to get the piston head 14 moving at the beginning of inspiration.

The electronic circuitry 22 may include safety features powered by battery in the event of power failure. For example, an alarm may be made to sound in the event that there is a power failure, a failure of pressure to cycle for a preset period, an excess pressure or a large inspired volume.

A variety of gauges, read-outs and recorders may be provided to display, store or compilate a variety of parameters, including breath by breath or moving averages, of tidal volume, ventilation frequency, inspiratory duration, duty cycle (inspiratory duration/cycle duration) and respiratory system compliance.

Turning now to FIG. 11, there is illustrated therein another preferred embodiment of the invention, which is a much simplified version of the embodiment of FIG. 8, and currently is the best mode known to the applicant for carrying the invention (PAV) into effect. A low inertia, low resistance rolling seal piston 201 freely moves within a chamber 202. The chamber 202 receives gas through a one-way valve with an appropriate opening pressure level 203 during the exhalation phase while, during the inhalation phase, gas moves from the chamber 202 to patient 208 through another one-way valve 204. The piston 201 is coupled to the coil of a linear drive motor 205, which itself moves freely within a fixed magnet 206. The coil 205 pushes or pulls on the piston 201 in proportion to the magnitude of the drive potential supplied to the coil 205 via a cable 207. Clearly, any other type of bellows-motor combination would be suitable, provided that the requirement is satisfied that there is permitted a free flow of gas to the patient under a gradient generated by the patient. This requirement can be met either through the inherent mechanical properties (i.e. low inertia, low resistance) of the bellow-motor combinations or through appropriate servo-control of bellows position, as in prior art.

The rate of flow of gas from the chamber 202 to the patient 208 is measured by a flow meter 209 mounted on the inhalation conduit 210 which generates an instantaneous flow signal. Alternatively, the rate of gas flow can be measured using a velocity transducer that monitors the rate of piston movement (not shown). The position of the piston 201 is also monitored using a potentiometer 211 or other appropriate device, as described above with respect to FIGS. 8 to 10.

The instantaneous flow signal (i.e., an electrical signal indicative of the instantaneous rate of flow of gas through the inhalation conduit 210) is conditioned through an externally adjustable gain control 212. This is the equivalent of $K_2$ in equation 3 above. The amplification may be constant or variable to allow for non-linear behaviour of the pressure-flow relation of patient and/or external tubing. The instantaneous flow signal is also integrated using an integrator 213 to provide a signal corresponding to instantaneous inhaled volume 214 (i.e., an electrical signal indicative of the instantaneous volume of flow of gas through the inhalation conduit 210). The latter is also conditioned through an externally adjustable gain control 215. This is the equivalent of $K_1$ in equation 3 above and again may be constant or variable to allow for non-linear elastic properties of the respiratory system. The amplified flow and volume signals 216, 217 are summed using a summing amplifier 218, to generate a composite output signal. The summing amplifier may also receive other inputs 219 to permit the unit to be operated in a non-proportonal assist mode. These additional inputs are described below.

A switch mechanism 220 channels the output of the summing amplifier 218 to the motor 205 during the inhalation phase and the later part of the exhalation phase. During the early part of the exhalation, the switch 220 channels instead a constant negative voltage 221 to return the piston 201 to a preset location, as judged by the potentiometer signal 211. In either case, the command signal 222 is first suitably amplified using a power amplifier 223 and power supply 224.

An exhalation tube 225 and exhalation valve 226 insure gas flow from patient to the ambient atmosphere during the exhalation phase. Any of a variety of commercially available exhalation valves can be used. The exhalation valve 226 is opened or closed according to its valve control mechanism 228.

A differential pressure transducer 227 measures the pressure gradient between a point upstream and a point downstream from the one-way valve 204 that directs flow on the inhalation line 210. The downstream point is preferably as close as possible to the patient to enhance the sensitivity of the transducer 227 to flow, while the upstream point may be conveniently located at the chamber 202. The inhalation phase is defined as any time during which the pressure upstream is higher than the pressure at the point nearer the patient. The exhalation phase is when pressure on the patient side of the valve 204 is higher than in the chamber 202. The output of the differential transducer 227 is channeled to the exhalation valve control mechanism 228 and to the switching mechanism 220 for the motor drive 205. At transition from inhalation to exhalation, as defined by transducer 227 output, the integrator 213 is reset to return the volume signal 214 to zero, in preparation for the next cycle.

Other inputs 219 to the summing amplifier 218 may include any of a variety of functions. Two preferred functions are a constant voltage, to provide continuous positive airway pressure (CPAP) if desired, and an input designed to cancel out the effect of inhalation tube resistance. In the latter case, the output of the differential transducer 227 is channeled to the summing amplifier 218 after suitable amplification and rectification (positive gradients from chamber to patient only). In this fashion, the piston generates a positive pressure component that equals the pressure gradient between chamber and patient, thereby essentially eliminating the resistive effect of the tubing at all flow rates.

Other inputs 219 may also include back-up functions, for example repetitive ramp or square wave voltage vs time functions to insure ventilation in the event of apnea. Alternatively, through these other inputs, manufacturers may wish to add other types of conventional ventilation methods in machines that deliver PAV, so that these additional methods, for example, airway pressure release ventilation (APRV) or synchronized intermittent mandatory ventilation (SIMV) or pressure support (PS), may be used jointly or alternately with PAV.

At the beginning of the exhalation phase, the piston 201 retracts under the influence of the negative voltage 221, acquiring fresh gas of a desired composition through the one-way valve 203 until it reaches a preset level. The switching mechanism 220 then disconnects the negative voltage and channels the output of the summing amplifier 218 to the motor 205. At this point, the conditioned flow signal 216 is zero and the conditioned volume signal 217 is also zero as a result of integrator 213 resetting. The only drive is from other inputs 219. In the event a constant voltage is applied via other inputs 219, the motor 205 will pressurize the piston 201 to a constant level in preparation for the next inhalation. The level of constant pressure is typically set to be just below the level of desired positive end expiratory pressure (PEEP), as determined by the exhalation valve control or other suitable PEEP device. In this way, flow begins from chamber to patient as soon as airway pressure decreases below the PEEP level. Once flow begins, the output of the summing amplifier changes according to the sum of the conditioned flow 216 and volume 217 signals and the constant voltage, if any, via other inputs 219. This causes the pressure in the chamber 202 to rise. As discussed in detail above, so long as the gain factors for flow 212 and volume 215 are less than the values of resistance and patient elastance, the chamber pressure is not adequate by itself to entirely support the elastic recoil and resistive pressure losses and the patient is, therefore, contributing to the total pressure, and flow and volume remain responsive to patient effort. Once the patient terminates his own respiratory effort, there is accordingly not enough pressure to sustain the elastic recoil of the respiratory system. Pressure in the airway rises above chamber pressure and this, via the differential pressure transducer 227, causes the opening of the exhalation valve 226, resetting of the integrator 223 and hence loss of chamber pressure and the cycle is repeated.

Apart from its simplicity and ease of operation, this design has the distinct advantage of making it unnecessary to utilize servo-feedback of pressure output, as is necessary in the embodiment of FIGS. 8 to 10.

SUMMARY OF DISCLOSURE

In summary of this disclosure, the present invention provides a novel ventilation unit and ventilating procedure which are able to deliver air to a patient in proportion to patient ongoing inspiratory effort (Proportinoal Assist Ventilation, PAV). Modifications are possible within the scope of this invention.

What I claim is:

1. A method for providing breathing assistance in proportion to patient ongoing inspiratory effort, which comprises:
   providing a free flow of gas from a gas delivery system to a patient in response to a pressure gradient generated by patient inspiratory effort,
   determining the rate and volume of flow of said gas to said patient,
   independently amplifying signals corresponding to said determined rate and volume of flow, and
   providing a pressure assist to said gas in proportion to the sum of said determined and amplified rate and volume of flow.

2. The method of claim 1, wherein said pressure assist is determined by the equation:

$$P_{vent} = K_1 V + K_2 \dot{V}$$

where $P_{vent}$ is the magnitude of the pressure assist, $K_1$ is a gain factor applied to a variable ongoing volume signal $V$ and $K_2$ is a gain factor applied to a variable ongoing flow-signal $\dot{V}$.

3. The method of claim 2 wherein non-linear functions are employed in place of $K_1$ and $K_2$.

4. The method of claim 1 wherein said pressure assist is determined by the equation:

$$P_{vent} = A \cdot P_{mus}$$

where $P_{vent}$ is the magnitude of the pressure assist, A is an independent factor which determines the proportionally between the pressure assist and patient generated pressure, and $P_{mus}$ is the estimated instantaneous patient generated pressure determined by the equation:

$$P_{mus} = V \cdot E_{rs} + \dot{V} \cdot R_{rs} - P_{vent}$$

where $V$ is the magnitude of the variable ongoing volume signal, $\dot{V}$ is the magnitude of the variable ongoing flow signal, $E_{rs}$ is the elastance of the respiratory system of the patient and $R_{rs}$ is the resistance against which the respiratory system of the patient is operating.

5. The method of claim 1 wherein said rate and volume of flow are determined by continuously sensing the movement of gas to the patient and generating an electrical signal corresponding in magnitude to each of the sensed rate and volume of gas, continuously separately amplifying each signal to a degree required to provide the pressure assist and providing a summed signal combining each of said amplified signals, and continuously applying said summed signal to said gas delivery system, thereby to provide said pressure assist.

6. The method of claim 5 wherein said movement of gas is sensed to generate an electrical signal corresponding to the rate of flow of gas through a tube connecting said gas delivery system to the patient, and said electrical signal is integrated to provide a further electrical signal corresponding to the volume of flow through said tube.

7. The method of claim 6 wherein said gas delivery system comprises bellows means and an electrical motor operatively connected to said bellows means to generate a pressure corresponding in magnitude to the magnitude of the summed signal applied to said electrical motor.

8. The method of claim 1 wherein said gas delivery system develops negative pressure to assist patient's breathing through the application of negative pressure to a body surface of the patient.

9. The method of claim 1 when used in conjunction with a method of ventilatory assist employing a predetermined relationship of pressure, flow and/or volume versus time, including continuous positive airway pressure (CPAP), intermittent mandatory ventilation (IMV), pressure support ventilation (PSV), and airway pressure release ventilation (APRV).

10. Apparatus for delivering proportional assist ventilation to a patient, comprising:
   means for delivering a free flow of gas to said patient in response to patient inhalatory effort,
   means operatively connected to said gas delivery means for generating pressure in said free flow of gas in response to an electrical command signal,
   detection means for detecting the instantaneous volume and rate of gas flow to said patient and for generating a separate electrical signal corresponding in magnitude to each of said detected values,
   means for selectively applying amplification to each of said electrical signals, and
   means for generating said electrical command signal to said pressure generating means in proportion to the sum of said amplified electrical signals corresponding in magnitude to said instantaneous rate and volume of flow.

11. The apparatus of claim 10 wherein said gas delivery means comprises bellows means and said gas pressure generating means comprises an electrical drive motor operatively connected to said bellows means.

12. The apparatus of claim 11 wherein said bellows means comprises a rolling seal piston.

13. The apparatus of claim 10, wherein said detection means comprises flow rate sensing means operatively connected to a pipe joining said bellows means to a patient for generating an electrical signal indicative of the instantaneous rate of flow of gas through said pipe and electrical circuit means for generating an electrical signal indicative of volume flow through said pipe from said electrical signal indicative of gas flow rate as said detected instantaneous value of flow volume.

14. The apparatus of claim 13, wherein said means for generating an electrical command signal comprises summing means for summing amplified electrical signals of said volume and gas flow rates, and including means for applying said command signal to said electrical motor means, thereby to provide a ventilatory assist to said patient corresponding to the magnitude of said summed signal.

15. The apparatus of claim 10 adapted to deliver ventilatory assist in the form of negative pressure intended for application to a body surface.

16. The apparatus of claim 10, including electrical circuit means to override said means for generating said electrical command signal to provide an alternative command signal corresponding to an operator predetermined relationship of pressure, flow and/or volume versus time, including continuous positive airway pressure (CPAP), intermittent mandatory ventilation (IMV), pressure support ventilation (PSV), and airway pressure release ventilation (APRV).

* * * * *